United States Patent
Dasbach

(10) Patent No.: US 10,159,804 B2
(45) Date of Patent: Dec. 25, 2018

(54) REUSE PREVENTION MECHANISM

(71) Applicant: SANOFI-AVENTIS DEUTSCHLAND GMBH, Franfurt am Main (DE)

(72) Inventor: Uwe Dasbach, Frankfurt am Main (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 322 days.

(21) Appl. No.: 14/906,596

(22) PCT Filed: Jul. 17, 2014

(86) PCT No.: PCT/EP2014/065419
§ 371 (c)(1),
(2) Date: Jan. 21, 2016

(87) PCT Pub. No.: WO2015/011021
PCT Pub. Date: Jan. 29, 2015

(65) Prior Publication Data
US 2016/0151587 A1    Jun. 2, 2016

(30) Foreign Application Priority Data

Jul. 22, 2013 (EP) .................... 13177489

(51) Int. Cl.
*A61M 5/32* (2006.01)
*A61M 5/50* (2006.01)

(52) U.S. Cl.
CPC ........ *A61M 5/3221* (2013.01); *A61M 5/3205* (2013.01); *A61M 5/3297* (2013.01);
(Continued)

(58) Field of Classification Search
CPC .............. A61M 5/3205; A61M 5/3297; A61M 5/3298; A61M 5/50; A61M 5/5086;
(Continued)

(56) References Cited

U.S. PATENT DOCUMENTS

| 5,873,462 | A | 2/1999 | Nguyen et al. | |
| 7,134,550 | B2 * | 11/2006 | Groth | A61M 5/002 206/366 |
| 2003/0078543 | A1 * | 4/2003 | Bergeron | A61M 5/002 604/192 |

FOREIGN PATENT DOCUMENTS

| EP | 2514457 | 10/2012 |
| EP | 2517744 | 10/2012 |

(Continued)

OTHER PUBLICATIONS

International Search Report and Written Opinion in International Application No. PCT/EP2014/065419, dated Oct. 6, 2014, 9 pages.
(Continued)

*Primary Examiner* — Kevin C Sirmons
*Assistant Examiner* — Leah Swanson
(74) *Attorney, Agent, or Firm* — Fish & Richardson P.C.

(57) ABSTRACT

A reuse prevention mechanism includes a guidance arm with a pin engaged in a guidance contour adapted to control movement of the guidance pin, and a blocking part adapted to block access to a needle in a fourth position of the reuse prevention mechanism. The guidance contour is adapted to constrict linear movement of the reuse prevention mechanism in a direction from a first position to a third position.

18 Claims, 5 Drawing Sheets

(52) U.S. Cl.
CPC ............ *A61M 5/50* (2013.01); *A61M 5/5086* (2013.01); *A61M 2005/3226* (2013.01)

(58) Field of Classification Search
CPC .. A61M 2005/3223; A61M 2005/3226; A61M 5/3295; B65D 83/02; B65D 83/0454; B65D 85/24
See application file for complete search history.

(56) References Cited

FOREIGN PATENT DOCUMENTS

GB            2459772      11/2009
WO     WO 2009136193 A1 *   11/2009             A61M 5/002

OTHER PUBLICATIONS

International Preliminary Report on Patentability in International Application No. PCT/EP2014/065419, dated Jan. 26, 2016, 6 pages.

* cited by examiner

REUSE PREVENTION MECHANISM

CROSS-REFERENCE TO RELATED APPLICATIONS

This application is a U.S. national stage application under 35 USC § 371 of International Application No. PCT/EP2014/065419, filed on Jul. 17, 2014, which claims priority to European Patent Application No. 13177489.5, filed on Jul. 22, 2013, the entire contents of which are incorporated herein by reference.

TECHNICAL FIELD

The invention relates to a reuse prevention mechanism for preventing re-use of injection needles.

BACKGROUND OF THE INVENTION

Patients suffering from diseases like diabetes have to frequently self-administer injections. Injection devices like auto-injectors or pen injectors have been developed to facilitate self-administering injections. Typically, such injection devices are re-usable and refitted with sterile injection needle assemblies to minimize the risk of infections.

Portable needle storage devices like needle magazines or needle dispensers contain a plurality of such sterile injection needle assemblies that are adapted to be mounted to the injection devices. The needle storage devices supplement the injection devices to facilitate safe self-administration of the medicament. Additionally, the needle storage device may be used as a disposal container for used injection needles to reduce the risk of accidental needle stick injuries caused by contaminated injection needles.

There remains a need for a mechanism for preventing re-use of injection needles.

SUMMARY OF THE INVENTION

Some aspects of the invention relate to a reuse prevention mechanism for preventing re-use of injection needles.

Preferred embodiments of the invention are given in the dependent claims.

In an exemplary embodiment, a reuse prevention mechanism for preventing reuse of an injection needle comprises a guidance arm with a pin engaged in a guidance contour adapted to control movement of the guidance pin, and a blocking part adapted to block access to a needle in a fourth position of the reuse prevention mechanism. The guidance contour is adapted to constrict linear movement of the reuse prevention mechanism in a direction from a first position to a third position. The guiding contour comprises a one-way feature adapted to constrict linear movement of the reuse prevention mechanism in the direction from the first position to the third position and adapted to allow linear movement in an opposite direction from the third position to the first position.

In an exemplary embodiment, the reuse prevention mechanism further comprises a detection arm for detecting presence of a needle in a needle cavity. The detection arm is prevented from entering the needle cavity by a needle present in the needle cavity and allowed to enter the needle cavity otherwise, thereby moving the reuse prevention mechanism in such a manner that the guidance pin moves into a second position circumventing the one-way feature.

In an exemplary embodiment, the reuse prevention mechanism further comprises a linear bearing defining an axis in the direction (D) which the reuse prevention mechanism may be rotated about for allowing circumvention of the one-way feature by the pin.

In an exemplary embodiment, the direction is aligned substantially tangential with respect to a longitudinal axis of the needle cavity.

In an exemplary embodiment, the detection arm comprises a protrusion with a ramp for entering the needle cavity and for allowing a needle head of the needle to displace the protrusion from the needle cavity.

In an exemplary embodiment, the reuse prevention mechanism further comprises at least one spring arranged to generate a force to drive the reuse prevention mechanism in the direction and/or to apply a torque to the reuse prevention mechanism in a sense of rotation biasing the detection arm into the needle cavity and biasing the pin towards the second position.

In an exemplary embodiment, the guidance contour is shaped to allow movement of the pin from the first position to the second position, and the movement comprises rotation in the sense and linear movement in the direction.

In an exemplary embodiment, the guidance contour is shaped to allow movement of the pin from the second position to the third position on displacement of the detection arm from the needle cavity by insertion of a needle into the needle cavity. The movement comprises rotation against the sense and linear movement in the direction. A surface on the reuse prevention mechanism is arranged to abut an injection device attached to the needle thus limiting the linear movement and defining the third position. The guidance contour is shaped to allow linear movement of the pin from the third position to the fourth position on removal of the injection device from the needle cavity thus removing the obstruction to the surface and allowing the blocking part to partially move over a cavity opening of the needle cavity.

In an exemplary embodiment, the blocking part comprises a sign colour visually indicating the fourth position.

In an exemplary embodiment, the reuse prevention mechanism further comprises a nose adapted to mesh with a cog on a needle cavity magazine arranged as a needle chain, in which a plurality of needle cavities is arranged. The nose is adapted to engage the cog on movement of the needle cavity magazine for feeding a new needle cavity such that the reuse prevention mechanism is linearly moved from the fourth position through the third position to the first position.

In an exemplary embodiment, the guidance arm is flexible and wherein at least one of the one way feature and the pin is ramped for deflecting the pin around the one-way feature on linear movement of the reuse prevention mechanism from the third position to the first position.

In an exemplary embodiment, a needle storage arrangement according to the present invention comprises a case with an access opening, a needle cavity magazine with a plurality of needle cavities arranged in the case, and a reuse prevention mechanism according to the present invention arranged between the access opening and one of the needle cavities aligned with the access opening. The needle cavity magazine is arranged as a circular needle chain such that the cog follows a circular path. The cog is adapted to disengage the nose and release the reuse prevention mechanism due to the diverging circular path of the cog and the linear path of the nose.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

Corresponding parts are marked with the same reference symbols in all figures.

DETAILED DESCRIPTION OF PREFERRED EMBODIMENTS

Figure 1:
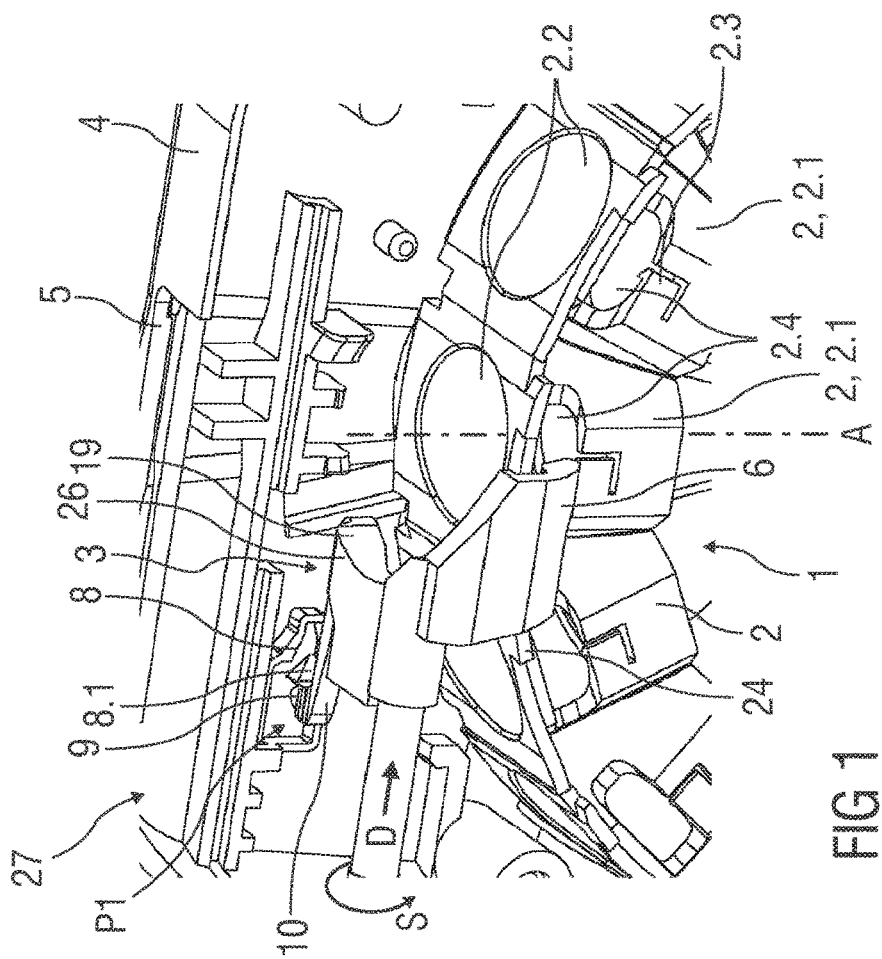
FIG. 1 is a schematic view of a needle cavity magazine with a plurality of needle cavities and a reuse prevention mechanism in a case, wherein the reuse prevention mechanism is in an initial first position.
Figure 2:
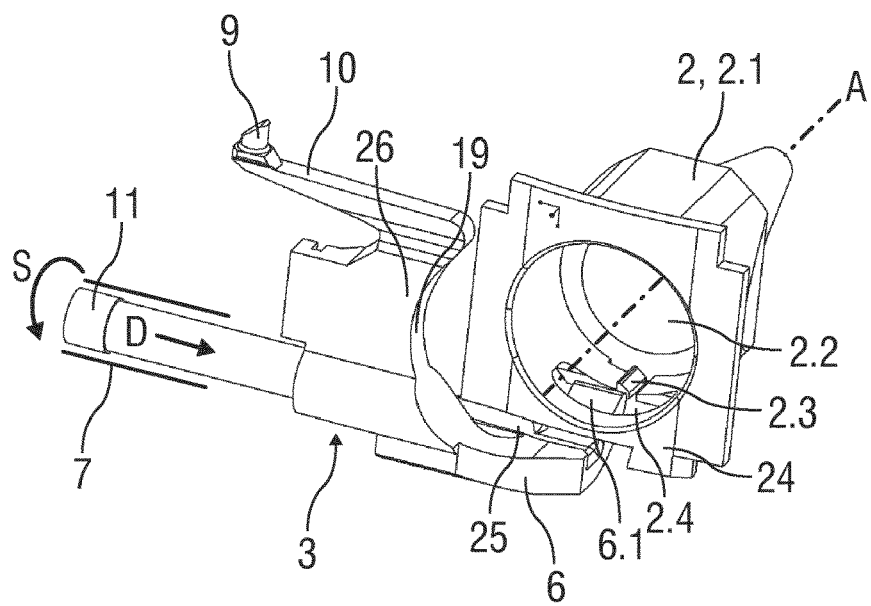
FIG. 2 is a schematic detail view of one of the needle cavities and the reuse prevention mechanism.

FIG. 1 is a schematic view of a needle storage arrangement 27 comprising a needle cavity magazine 1 with a plurality of needle cavities 2 and a reuse prevention mechanism 3 in a case 4, wherein the reuse prevention mechanism 3 is in an initial first position P1. FIG. 2 is a schematic detail view of one of the needle cavities 2 and the reuse prevention mechanism 3. The needle cavity 2 comprises a hollow body 2.1 adapted to receive an injection needle with a needle head (cf. FIG. 4). A cavity opening 2.2 in the body 2.1 allows for inserting and removing the injection needle with the needle head. The body 2.1 comprises a compliant clip arm 2.3 with a ledge radially inwardly protruding into the interior of the body 2.2 when the clip arm 2.3 is relaxed. The ledge comprises a ramp having an obtuse angle in one sense of rotation and a stop having an acute angle in an opposite sense of rotation. A lateral opening 2.4 is arranged in the body 2.1.

The needle cavity magazine 1 comprising the plurality of needle cavities 2 may be arranged as a needle chain such that the needle cavities 2 may be subsequently aligned with the access opening 5 by advancing the needle cavity magazine 1. In an exemplary embodiment each needle cavity 2 may be connected to two adjacent needle cavities 2, e.g. by a live hinge, such that the needle cavities 2 form a needle cavity magazine 1 in the shape of a needle chain.

The reuse prevention mechanism 3 for controlling access to the needle cavities 2 in the needle cavity magazine 1 is arranged to prevent multiple uses of injection needles. The reuse prevention mechanism 3 is adapted to be placed between an access opening 5 in the case 4 and one of the needle cavities 2 aligned with the access opening 5. The reuse prevention mechanism 3 comprises a detection arm 6 that is guided by a linear bearing 7. The linear bearing 7 defines an axis which the reuse prevention mechanism 3 may be rotated about. This axis runs in a direction D substantially tangential with respect to a longitudinal axis A of the needle cavity 2, which is respectively aligned with the access opening 5. The detection arm 6 comprises a protrusion 6.1 with a ramp.

Figure 3:
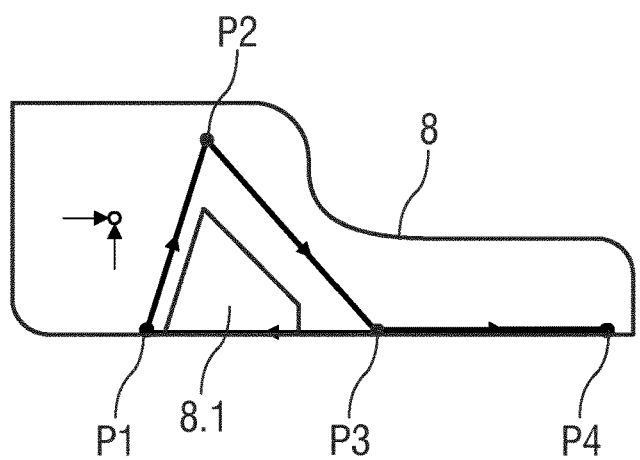
FIG. 3 is a schematic view of a guidance contour adapted to control a guidance pin of the reuse prevention mechanism.

A guidance contour 8, which may be implemented e.g. in the case 4, is adapted to guide a pin 9 laterally arranged on a flexible guidance arm 10. FIG. 3 is a schematic view of the guidance contour 8 adapted to control movement of the guidance pin 9 of the reuse prevention mechanism 3. The guidance contour 8 comprises a one-way feature 8.1 with a substantially triangular profile preventing movement of the guidance pin 9 from a first position P1 directly to a third position P3 in the direction D but allowing movement in the opposite direction from the third position P3 directly to the first position P1.

A pre-stressed spring 11, e.g. a compression spring, is arranged to generate a force to drive the detection arm 6 in the direction D. Furthermore, the spring 11 applies a torque to the detection arm 6 in a sense S of rotation biasing the protrusion 6.1 of the detection arm 6 through the lateral opening 2.4 into the needle cavity 2.

Figure 4:
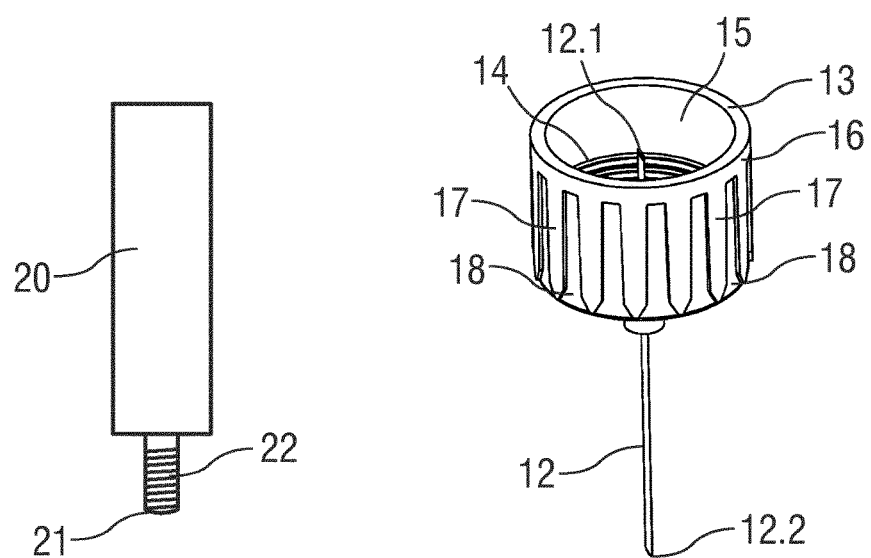
FIG. 4 is a schematic perspective view of an exemplary embodiment of an injection needle and a drug delivery device.

FIG. 4 is a schematic perspective view of an exemplary embodiment of an injection needle 12 and an injection device 20. The injection needle 12 comprises a needle head 13. The needle head 13 substantially has the shape of a hollow cylinder closed at one end, in which the needle 12 is coaxially arranged, such that a proximal tip 12.1 of the needle 12 adapted to pierce a septum 21 on the injection device 20 or cartridge protrudes into the needle head 13 and a distal tip 12.2 of the needle 12 adapted to penetrate an injection site extends from the needle head 13. A thread 14 is arranged on an inner surface 15 of the needle head 13. The thread 14 is adapted to interface with a corresponding thread 22 on the injection device 20. An outer surface 16 of the needle head 13 may comprise a number of longitudinal fins 17 spaced from each other by gaps 18 and distributed around the circumference of the needle head 13, such that fins 17 and gaps 18 alternate. In an exemplary embodiment the fins 17 are uniformly spaced. The fins 17 and gaps 18 may interface with the compliant clip arm 2.3 in the needle cavity 2 which may be adapted to constrain rotation of the needle head 13 within the cavity 2 when the needle 12 is being screwed onto the injection device 20 but to allow rotation of the needle head 13 within the cavity 2 when a predetermined force of the fin 17 on the compliant clip arm 2.3 is exceeded thus preventing overwinding of the screw threads 14, 22 of the needle 12 and the injection device 20 and produces a haptic and acoustic signal that the screw threads 14, 22 are tightened. The compliant clip arm 2.3 may be adapted to prevent rotation of the needle head 13 within the cavity 2 when the needle 12 is being unscrewed from an injection device 20.

The reuse prevention mechanism 3 is adapted to allow inserting an injection device 20, e.g. a pen injector to pick up a new needle 12 and disables the reuse of one-time discarded needles 12. By removing the needle 12 of the needle cavity 2, reuse prevention is activated. After deposition of the used needle 12 the reuse prevention mechanism 3 blocks access for the injection device 20. The procedure restarts when an unused needle 12 is carried towards the access opening 5, e.g. by rotating the needle cavity magazine 1.

In an initial state, as illustrated in FIG. 1, the guidance pin 9 stands in a first position P1 of the guidance contour 8. As long as the needle 12 remains in the needle cavity 2, the protrusion 6.1 of the detection arm 6 is prevented from entering the needle cavity 2 by laterally abutting the needle head 13. To activate the reuse prevention mechanism 3, the injection device 20 is inserted into the needle cavity 2, screwed on the needle thread 14 and pulled out of the case 4.

Figure 5:
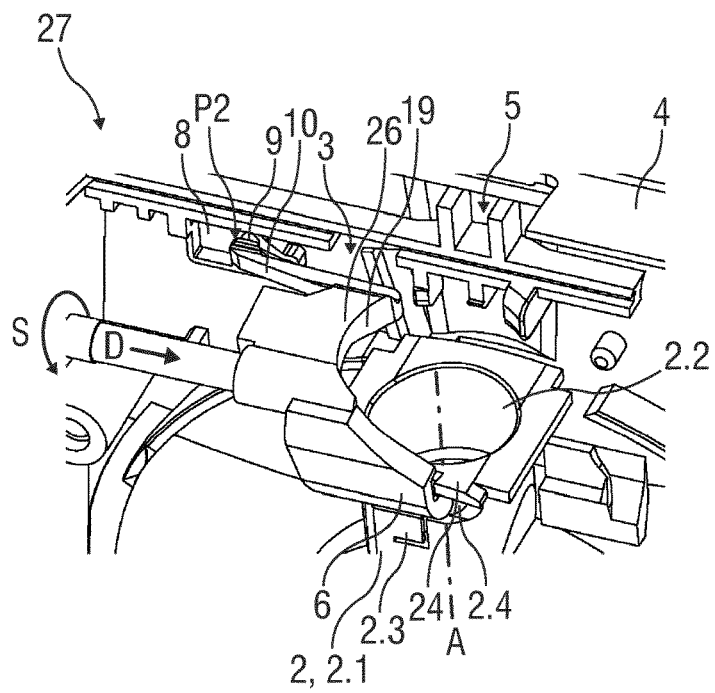
FIG. 5 is a schematic view of one of the needle cavities and the reuse prevention mechanism in a second position.
Figure 6:
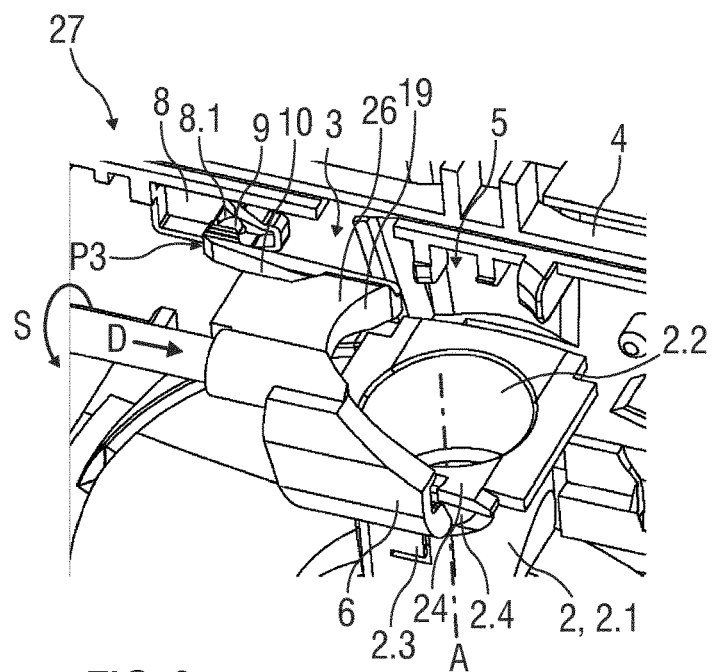
FIG. 6 is a schematic view of one of the needle cavities and the reuse prevention mechanism in a third position.
Figure 7:
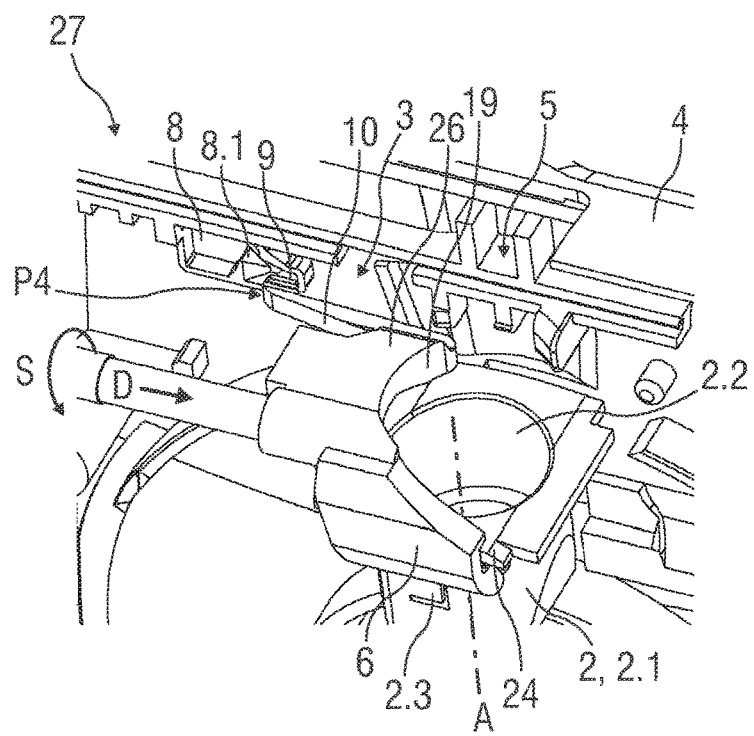
FIG. 7 is a schematic view of one of the needle cavities and the reuse prevention mechanism in a fourth position.

After taking out the injection device 20 and the needle 12, the protrusion 6.1 of the detection arm 6 is no longer blocked by the needle head 13 and, due to the torque from the spring 11, moves into the empty needle cavity 2. By this rotation, which is forced by the spring 11, the guidance pin 9 is moved within the guidance contour 8 from the first position P1 to a second position P2 thus circumventing the one-way feature 8.1 of the guidance contour 8. FIG. 5 is a schematic view of one of the needle cavities 2 and the reuse prevention mechanism 3 in the second position P2. In the second position P2 the injection device 20 with the attached needle 12 is still able to enter the needle cavity 2 due to the ramp on the protrusion 6.1 of the detection arm 6. When the injection device 20 is inserted again the needle head 13 passes and deflects the protrusion 6.1 out of the lateral opening 2.4. Hence the reuse prevention mechanism 3 rotates back against the sense S of rotation and the guidance pin 9 is moved into the previous height level as in the first position P1. However, due to the spring 11 biasing the reuse prevention mechanism 3 in the direction D and the guidance pin 9 being guided by the one-way feature 8.1 of the guidance contour 8, the reuse prevention mechanism 3 will slide into a third position P3, where the sliding movement is stopped by a surface 19 of a blocking part 26 of the reuse prevention mechanism 3 laterally contacting the injection device 20. FIG. 6 is a schematic view of one of the needle cavities and the reuse prevention mechanism 3 in the third position P3. The injection device 20 may be screwed off the needle 12 and subsequently be removed from the needle cavity 2 for the second time such that the surface 19 of the reuse prevention mechanism 3 is no longer blocked from moving further in the direction D. The reuse prevention mechanism 3 can thus slide into a final fourth position P4 with the blocking part 26 at least partially blocking the access opening 5 such that the injection device 20 cannot be re-inserted. FIG. 7 is a schematic view of one of the needle cavities 2 and the reuse prevention mechanism 3 in the fourth position P4. The reuse prevention mechanism 3 or its blocking part 26 visible in the access opening 5 in the fourth position P4 may comprise a sign colour (e.g. red), indicating the locking status to the user.

Figure 8:
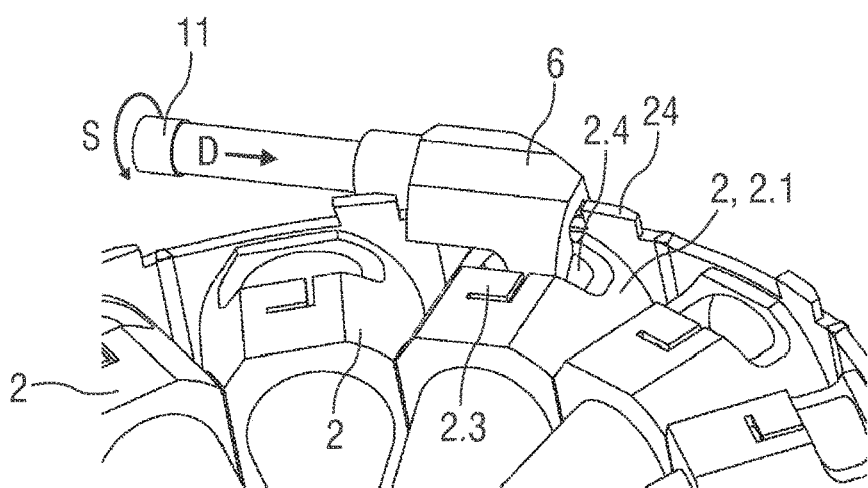
FIG. 8 is a schematic view of the needle cavity magazine with the plurality of needle cavities and a needle chain with a plurality of cogs for resetting the reuse prevention mechanism.

FIG. 8 is a schematic view of the needle cavity magazine 1 with the plurality of needle cavities 2 and a needle cavity magazine 1 in the shape of a circular needle chain with a plurality of cogs 24 for resetting the reuse prevention mechanism 3.

The needle cavity magazine 1 may comprise a plurality of cogs 24 arranged to be engaged by a drive (not illustrated) for conveying the needle cavity magazine 1. The cogs 24 on the needle cavity magazine 1 are adapted to mesh with a nose 25 on the inside of the detection arm 6. When the needle cavity magazine 1 rotates to place a new needle cavity 2 towards the access opening 5, the cog 24 pushes against the nose 25 and transports the reuse prevention mechanism 3 back to the first position P1. The detection arm 6 and the whole reuse prevention mechanism 3 can only move in and opposite the direction D due to the linear bearing 7. Furthermore, the detection arm 6 cannot rotate due to the guidance pin 9 being engaged to the guidance contour 8 and the needle head 13 blocking the protrusion 6.1. Thus, as the cog 24 engages the nose 25, the guidance pin 9 moves on the track from the fourth position P4 via the third position P3 to the first position P1. This movement is possible, as the guidance arm 10 is flexible and the shape of both—the guidance contour 8 and the guidance pin 9—is inclined in a resetting-direction, i.e. opposite the direction D. To release the mesh of cog 24 and nose 25, the reuse prevention mechanism 3 is moved further than the first position P1. As the cog 24 follows a circular path and the nose 25 follows a linear path, the paths diverge on sufficient movement of the cog 24 such that the cog 24 disengages the nose 25 and releases the reuse prevention mechanism 3. After being released, the reuse prevention mechanism 3 is moved to the first position P1 by the spring 11.

As a component of a needle cavity magazine 1 the reuse prevention mechanism 3 prevents multiple uses of injection needles 12. An easily noticeable barrier signalizes the user that a used needle 12 is not accessible any more. Compared to other systems the cutting point between needle 12 and needle cavity 2 is traced, which improves the deposition detection of the needle 12.

Those of skill in the art will understand that modifications (additions and/or removals) of various components of the apparatuses, methods and/or systems and embodiments described herein may be made without departing from the full scope and spirit of the present invention, which encompass such modifications and any and all equivalents thereof.

The invention claimed is:

1. A reuse prevention mechanism for preventing reuse of an injection needle, the reuse prevention mechanism comprising: a guidance arm with a pin engaged in a guidance contour adapted to control movement of the guidance pin; a blocking part adapted to block access to a needle in a fourth position of the reuse prevention mechanism; and a detection arm for detecting a presence of a needle in a needle cavity, wherein the detection arm is prevented from entering the needle cavity when a needle is present in the needle cavity and is allowed to enter the needle cavity otherwise, the detection arm configured to move the reuse prevention mechanism in such a manner that the guidance pin moves into a second position and circumvents a one-way feature, wherein the guidance contour is adapted to constrict linear movement of the reuse prevention mechanism in a direction from a first position to a third position, wherein the guiding contour comprises the one-way feature adapted to constrict linear movement of the reuse prevention mechanism in the direction from the first position to the third position and adapted to allow linear movement in an opposite direction from the third position to the first position.

2. The reuse prevention mechanism according to claim 1, further comprising a linear bearing defining an axis in a direction about which the reuse prevention mechanism may be rotated for allowing circumvention of the one-way feature by the pin.

3. The reuse prevention mechanism according to claim 1, wherein the direction from the first position to the third position is aligned substantially tangential with respect to a longitudinal axis of the needle cavity.

4. The reuse prevention mechanism according to claim 1, wherein the detection arm comprises a protrusion with a ramp for entering the needle cavity and for allowing a needle head of the needle to displace the protrusion from the needle cavity.

5. The reuse prevention mechanism according to claim 1, further comprising at least one spring arranged to generate a force to drive the reuse prevention mechanism in the direction from the first position to the third position and/or to apply a first torque to the reuse prevention mechanism in an axis of rotation biasing the detection arm into the needle cavity and biasing the pin towards the second position.

6. The reuse prevention mechanism according to claim 5, wherein the guidance contour is shaped to allow movement of the pin from the second position to the third position on displacement of the detection arm from the needle cavity by insertion of a needle into the needle cavity, the movement comprising linear movement and rotation in a direction opposite the first torque, wherein a surface on the reuse prevention mechanism is arranged to abut an injection device attached to the needle thus limiting the linear movement and defining the third position.

7. The reuse prevention mechanism according to claim 1, wherein the guidance contour is shaped to allow movement of the pin from the first position to the second position, the movement comprising rotation about an axis and linear movement in the direction from the first position to the third position.

8. The reuse prevention mechanism according to claim 1, wherein the guidance contour is shaped to allow movement of the pin from the second position to the third position on displacement of the detection arm from the needle cavity by insertion of a needle into the needle cavity, the movement comprising rotation and linear movement, wherein a surface on the reuse prevention mechanism is arranged to abut an injection device attached to the needle thus limiting the linear movement and defining the third position.

9. The reuse prevention mechanism according to claim 8, wherein the guidance contour is shaped to allow linear movement of the pin from the third position to the fourth position on removal of the injection device from the needle cavity thus removing an obstruction to the surface and allowing the blocking part to partially move over a cavity opening of the needle cavity.

10. The reuse prevention mechanism according to claim 1, wherein the blocking part comprises a color visually indicating the fourth position.

11. The reuse prevention mechanism according to claim 1, comprising a nose adapted to mesh with a cog on a needle cavity magazine arranged as a needle chain, in which a plurality of needle cavities is arranged, wherein the nose is adapted to engage the cog on movement of the needle cavity magazine for feeding a new needle cavity such that the reuse prevention mechanism is capable of being linearly moved from the fourth position through the third position to the first position.

12. The reuse prevention mechanism according to claim 1, wherein the guidance arm is flexible and wherein at least one of the one way feature and the pin is ramped for deflecting the pin around the one-way feature on linear movement of the reuse prevention mechanism from the third position to the first position.

13. A needle storage device, comprising:
a case with an access opening;
a needle cavity magazine with a plurality of needle cavities arranged in the case; and
the reuse prevention mechanism of claim 1 arranged between the access opening and one of the needle cavities aligned with the access opening.

14. The needle storage device according to claim 13, wherein the needle cavity magazine is arranged as a circular needle chain such that a cog follows a circular path, wherein the cog is adapted to disengage a nose adapted to mesh with the cog and release the reuse prevention mechanism due to a diverging circular path of the cog and a linear path of the nose.

15. A reuse prevention mechanism for preventing reuse of an injection needle, the reuse prevention mechanism comprising:
a guidance arm with a pin engaged in a guidance contour adapted to control movement of the guidance pin;
a blocking part adapted to block access to a needle in a fourth position of the reuse prevention mechanism; and
a nose adapted to mesh with a cog on a needle cavity magazine arranged as a needle chain, in which a plurality of needle cavities is arranged, wherein the nose is adapted to engage the cog on movement of the needle cavity magazine for feeding a new needle cavity such that the reuse prevention mechanism is capable of being linearly moved from the fourth position through the third position to the first position,
wherein the guidance contour is adapted to constrict linear movement of the reuse prevention mechanism in a direction from a first position to a third position, wherein the guiding contour comprises a one-way feature adapted to constrict linear movement of the reuse prevention mechanism in the direction from the first position to the third position and adapted to allow linear movement in an opposite direction from the third position to the first position.

16. A reuse prevention mechanism for preventing reuse of an injection needle, the reuse prevention mechanism comprising:
a guidance arm with a pin engaged in a guidance contour adapted to control movement of the guidance pin;
a blocking part adapted to block access to a needle in a fourth position of the reuse prevention mechanism; and
wherein the guidance contour is adapted to constrict linear movement of the reuse prevention mechanism in a direction from a first position to a third position, wherein the guiding contour comprises a one-way feature adapted to constrict linear movement of the reuse prevention mechanism in the direction from the first position to the third position and adapted to allow linear movement in an opposite direction from the third position to the first position, and
wherein the guidance arm is flexible and wherein at least one of the one way feature and the pin is ramped for deflecting the pin around the one-way feature on linear movement of the reuse prevention mechanism from the third position to the first position.

17. A reuse prevention mechanism for preventing reuse of an injection needle, the reuse prevention mechanism comprising: a guidance arm with a pin engaged in a guidance contour adapted to control movement of the guidance pin; a blocking part adapted to block access to a needle in a fourth position of the reuse prevention mechanism; and at least one spring arranged to generate a force to drive the reuse prevention mechanism in the direction from a first position to a third position and/or to apply a first torque to the reuse prevention mechanism in an axis of rotation biasing a detection arm into a needle cavity and biasing the pin towards a second position; wherein the guidance contour is adapted to constrict linear movement of the reuse prevention mechanism in a direction from the first position to the third position, wherein the guiding contour comprises a one-way feature adapted to constrict linear movement of the reuse prevention mechanism in the direction from the first position to the third position and adapted to allow linear movement in an opposite direction from the third position to the first position, and wherein the guidance contour is shaped to allow movement of the pin from the second position to the third position on displacement of the detection arm from the needle cavity by insertion of a needle into the needle cavity, the movement comprising linear movement and rotation in a direction opposite the first torque, wherein a surface on the reuse prevention mechanism is arranged to abut an injection device attached to the needle thus limiting the linear movement and defining the third position.

18. A needle storage device, comprising:
- a case with an access opening;
- a needle cavity magazine with a plurality of needle cavities arranged in the case; and
- a reuse prevention mechanism arranged between the access opening and one of the needle cavities aligned with the access opening, the reuse prevention mechanism comprising:
  - a guidance arm with a pin engaged in a guidance contour adapted to control movement of the guidance pin,
  - a blocking part, adapted to block access to a needle in a fourth position of the reuse prevention mechanism,
  - wherein the guidance contour is adapted to constrict linear movement of the reuse prevention mechanism in a direction from a first position to a third position, wherein the guiding contour comprises a one-way feature adapted to constrict linear movement of the reuse prevention mechanism in the direction from the first position to the third position and adapted to allow linear movement in an opposite direction from the third position to the first position, and
  - wherein the needle cavity magazine is arranged as a circular needle chain such that a cog follows a circular path, wherein the cog is adapted to disengage a nose adapted to mesh with the cog and release the reuse prevention mechanism due to a diverging circular path of the cog and a linear path of the nose.

* * * * *